(12) United States Patent
Fritzinger et al.

(10) Patent No.: US 9,301,674 B2
(45) Date of Patent: Apr. 5, 2016

(54) SELF-RETAINING RETRACTOR

(75) Inventors: Daniel D. Fritzinger, Warsaw, IN (US); Hill Hastings, Zionsville, IN (US)

(73) Assignee: BIOMET MANUFACTURING, LLC, Warsaw, IN (US)

( * ) Notice: Subject to any disclaimer, the term of this patent is extended or adjusted under 35 U.S.C. 154(b) by 181 days.

(21) Appl. No.: 13/295,171

(22) Filed: Nov. 14, 2011

(65) Prior Publication Data

US 2013/0123581 A1    May 16, 2013

(51) Int. Cl.
| | |
|---|---|
| *A61B 1/32* | (2006.01) |
| *A61B 17/02* | (2006.01) |
| A61B 17/28 | (2006.01) |
| A61B 17/80 | (2006.01) |

(52) U.S. Cl.
CPC .............. *A61B 1/32* (2013.01); *A61B 17/0206* (2013.01); *A61B 17/8061* (2013.01); *A61B 2017/2837* (2013.01)

(58) Field of Classification Search
CPC .. A61B 17/28–17/2955; A61B 17/02–17/0293
USPC .................................................. 600/201–235
See application file for complete search history.

(56) References Cited

U.S. PATENT DOCUMENTS

| | | | | |
|---|---|---|---|---|
| 5,931,777 A * | 8/1999 | Sava | | 600/213 |
| 6,042,540 A * | 3/2000 | Johnston et al. | | 600/213 |
| 6,196,969 B1 * | 3/2001 | Bester et al. | | 600/224 |
| 6,663,562 B2 * | 12/2003 | Chang | | 600/219 |
| 7,141,015 B2 * | 11/2006 | Ruane | | 600/220 |
| 7,976,463 B2 * | 7/2011 | Dewey et al. | | 600/210 |
| 8,226,554 B2 * | 7/2012 | McBride et al. | | 600/219 |
| 2003/0055319 A1 * | 3/2003 | Chang | | 600/210 |
| 2004/0002629 A1 * | 1/2004 | Branch et al. | | 600/210 |
| 2008/0077171 A1 * | 3/2008 | Blain et al. | | 606/190 |
| 2009/0192360 A1 | 7/2009 | Riess et al. | | |

OTHER PUBLICATIONS

Self-Retaining Retractors, Boss Instruments, Ltd., Neurosurgical and Orthopedic Instruments Catalog, pp. 140-144. © 2011.

Hohmann Retractors, Boss Instruments, Ltd. Neurosurgical and Orthopedic Instruments Catalog, pp. 501-502. © 2011.

* cited by examiner

*Primary Examiner* — Jan Christopher Merene
*Assistant Examiner* — Steven Cotroneo
(74) *Attorney, Agent, or Firm* — Schwegman Lundberg & Woessner, P.A.

(57) ABSTRACT

A tissue retractor generally includes a pair of arms that are pivotally coupled to each other and each have a finger grip portion on a first end and a working portion arranged on an opposite second end. Each of the second ends comprises an elongated shaft that extends along an axis. A pair of paddles each having a planar engagement body and a mounting portion are pivotally coupled to a corresponding elongated shaft. The paddles are selectively rotatable around the respective axes.

17 Claims, 6 Drawing Sheets

SELF-RETAINING RETRACTOR

FIELD

The present disclosure relates generally to tissue retractors, and more specifically relates to a tissue retractor having a pair of pivotally coupled arms that each include a tissue engaging member rotatably coupled at a distal end of the arm.

BACKGROUND

This section provides background information related to the present disclosure which is not necessarily prior art.

During many surgical procedures, it may be necessary to gain access to a bone or other internal area of a patient. For example, a surgeon may need to access a fractured bone to implant a bone plate or provide other means of fixation. In other examples, a surgeon may desire to access a bone in an effort to diagnose or treat other injuries related to the bone or surrounding tissue. In these examples, it is desirable to effectively displace the surrounding tissue in an effort to gain better access to the bone and surrounding area of interest. In this regard, in many instances it can become challenging and/or awkward to effectively manipulate surrounding tissue while making available the hands of a surgeon for other tasks such as manipulating the bone, implant, or using other surgical tools.

SUMMARY

This section provides a general summary of the disclosure, and is not a comprehensive disclosure of its full scope or all of its features.

A tissue retractor generally includes a pair of arms that are pivotally coupled to each other. Each arm can have a finger grip portion on a first end and a working portion arranged on an opposite second end. Each of the second ends comprises an elongated shaft that extends along an axis. A pair of paddles each having a planar engagement body and a mounting portion are pivotally coupled to a corresponding elongated shaft. The paddles are selectively rotatable around the respective axes.

According to other features, each paddle has a mounting hub that receives a corresponding elongated shaft. Each elongated shaft has an outer surface that is configured to slidably engage a corresponding inner surface of the mounting hub during rotation of the paddles. Rotation of the paddles around the respective axes is limited to a predetermined range.

According to still other features, the mounting hubs can each define a slot having terminal ends. A pin fixed to a corresponding elongated shaft is configured to ride along the slot and engage the terminal ends precluding further pivoting of the respective paddles. Each paddle can have a hook extending from a portion of the planar engagement body. The hook can extend at an angle relative to the planar engagement body.

According to other features, the tissue retractor can further comprise a ratchet assembly coupled between the pair of arms. The ratchet assembly can include a track coupled to one of the arms and a track follower extending from the other of the arms. The track follower can have an engaging body that cooperatively engages teeth formed on the track. The engaging body can be configured to selectively engage the teeth upon movement of the handle portions toward each other. Engagement of the engaging body with the teeth can inhibit movement of the handle portions away from each other. The engaging body can further include a releasing tab extending therefrom. Movement of the releasing tab can disengage contact between the engaging body and the teeth permitting movement of the handle portions away from each other.

A tissue retractor constructed in accordance to additional features of the present teachings can include a pair of arms that are pivotally coupled to each other. Each of the arms can have an elongated shaft that extends along an axis. A pair of tissue engaging members are each pivotally coupled to a corresponding elongated shaft. The pair of tissue engaging members have mounting portions that are journaled around a corresponding elongated shaft for rotation around the respective axes.

A method of retracting tissue according to one example of the present teachings can include inserting a pair of tissue engaging members into an incision prepared in a patient's body. A corresponding pair of handles can be advanced in directions relative to each other causing the respective pair of tissue engaging members to move away from each other. The pair of handles can be further advanced in directions relative to each other causing the respective pair of tissue engaging members to pivot about corresponding elongated shafts extending between the respective pair of handles and the tissue engaging members. According to additional features, the method can further include advancing the pair of handles such that a pin that is fixedly coupled to each elongated shaft is advanced along a slot formed along a mounting hub of a corresponding tissue engaging member. The pin is advanced until the pin engages a terminal end of the slot inhibiting further rotation of the tissue engaging member.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 6:
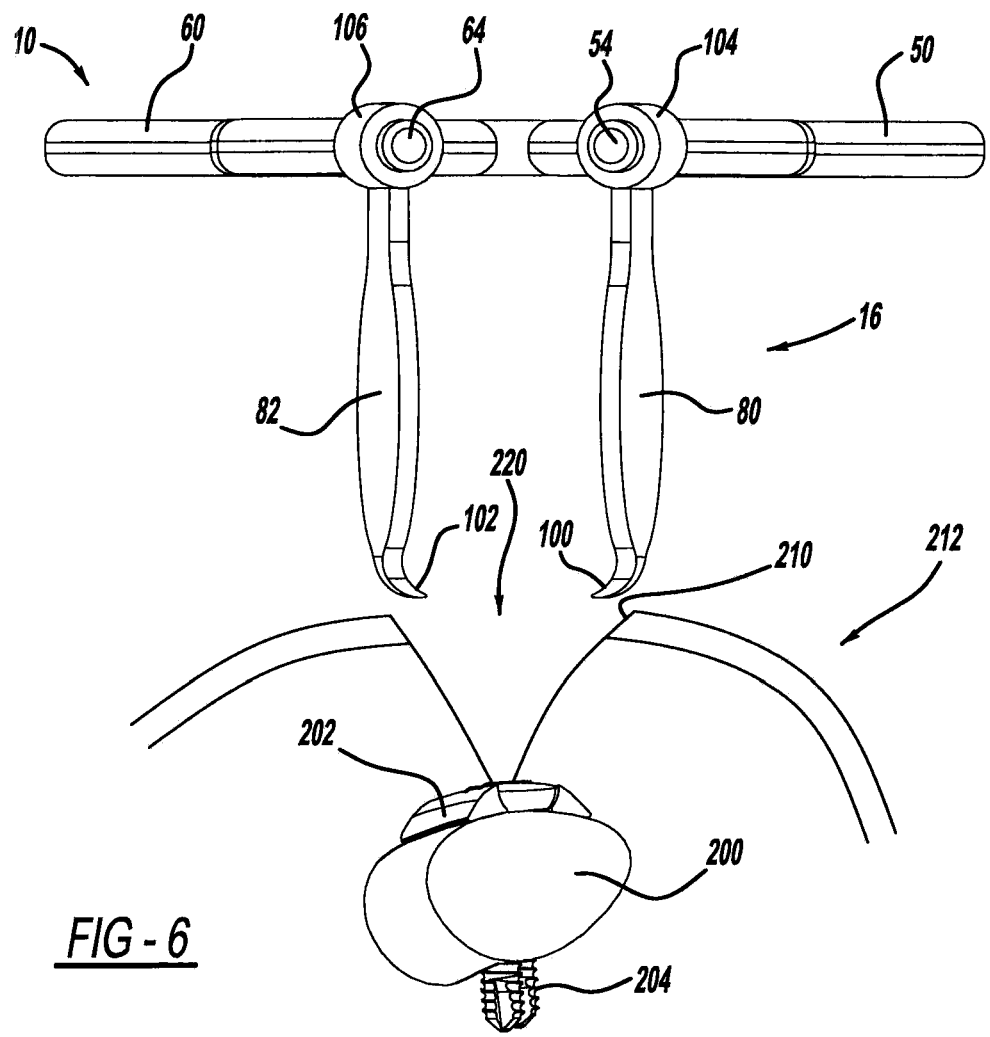
FIG. 6 is an end view of the tissue retractor of FIG. 1 and shown generally in an insertion position upon initial advancement of the tissue engagement members through an incision.
Figure 7:
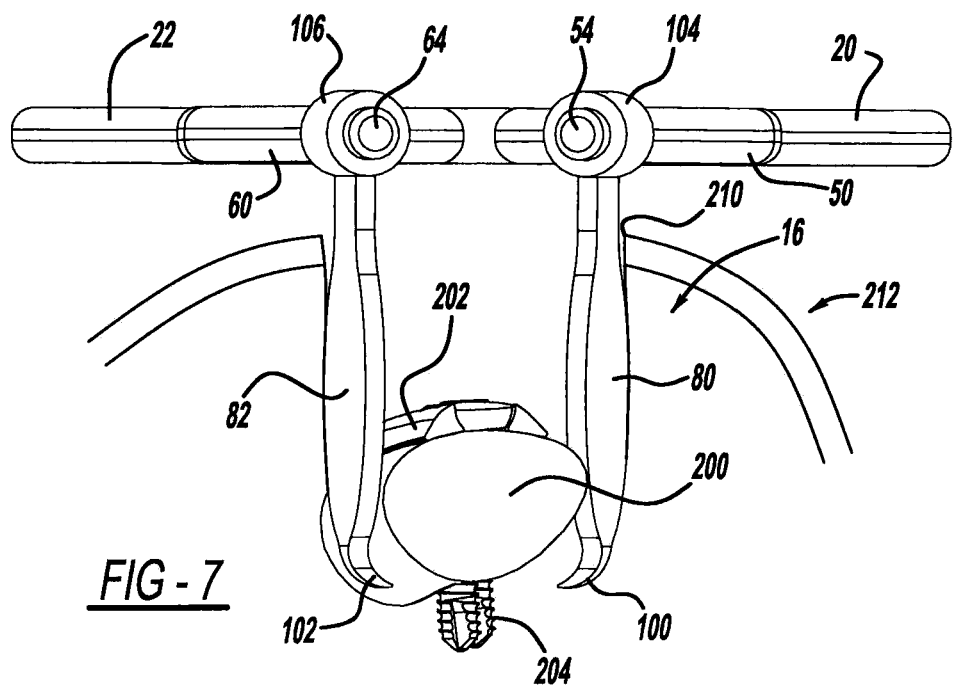
Figure 8:
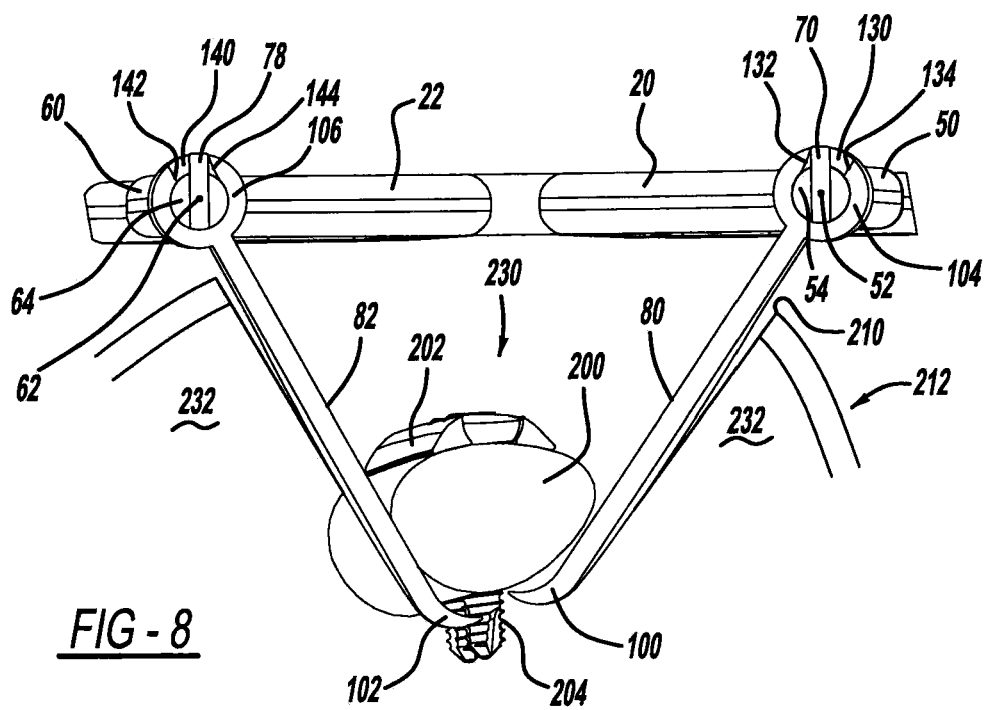

FIG. 7 is an end view of the tissue retractor of FIG. 6 and shown with the tissue retractor in the insertion position and further advanced toward engagement with the bone; and FIG. 8 is an end view of the tissue retractor of FIG. 7 and shown with the tissue engaging members rotated around the respective arms from the insertion position to the working position causing the surrounding tissue to be generally urged away from the bone to allow the surgeon relatively unimpeded access to the bone according to one example of the present teachings.

Corresponding reference numerals indicate corresponding parts throughout the several views of the drawings.

DETAILED DESCRIPTION

Example embodiments will now be described more fully with reference to the accompanying drawings. While the following description will be directed toward gaining access to a radius having a fracture to implant or modify a bone plate secured to the radius, the tissue retractor and related method according to the present teachings may be used to manipulate tissue for gaining access to other body parts such as bones, muscles, organs, etc.

Figure 1:
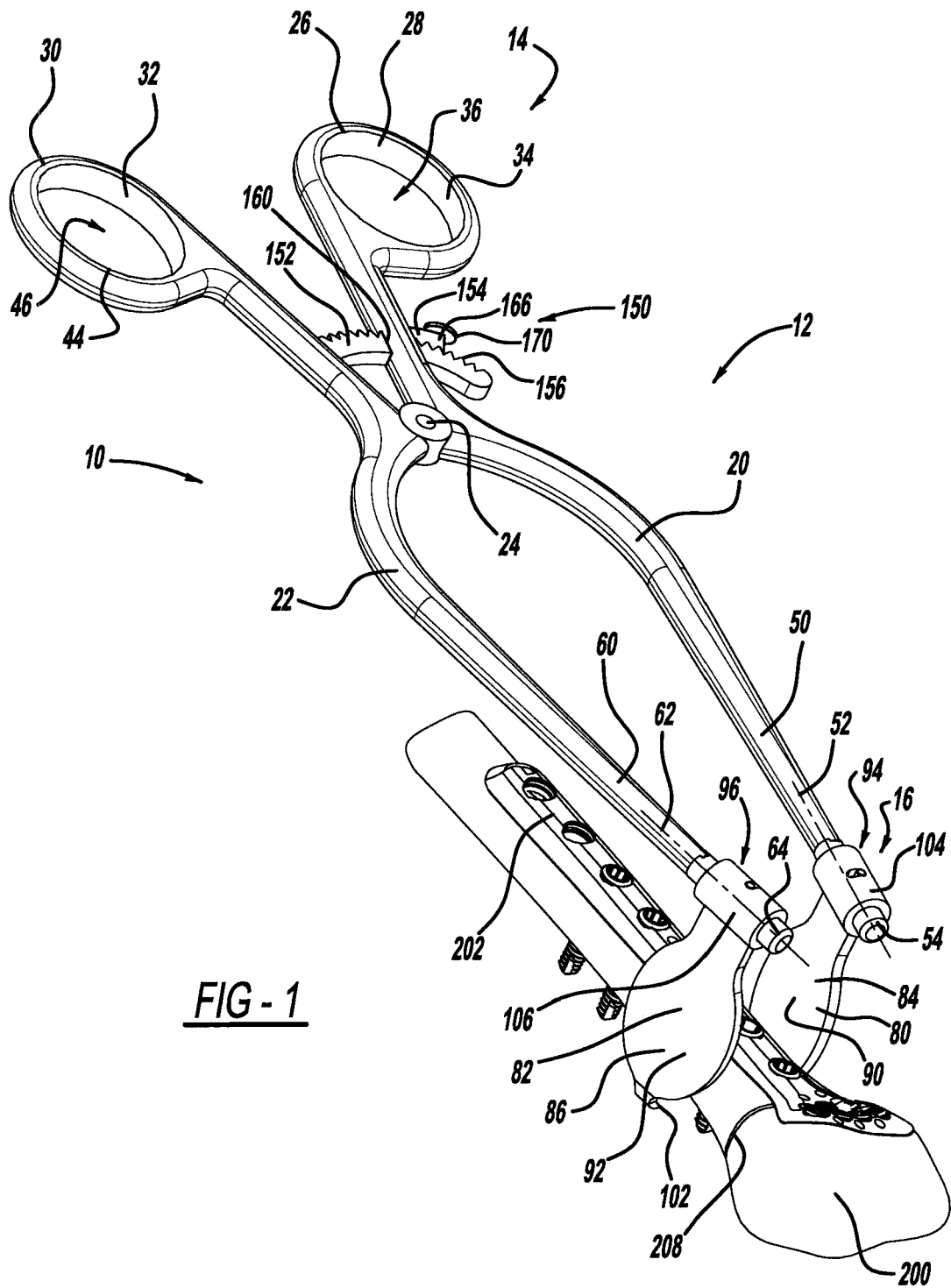
FIG. 1 is a perspective view of a tissue retractor constructed in accordance to one example of the present teachings and shown with a pair of tissue engaging members in an insertion position generally adjacent a bone.
Figure 2:
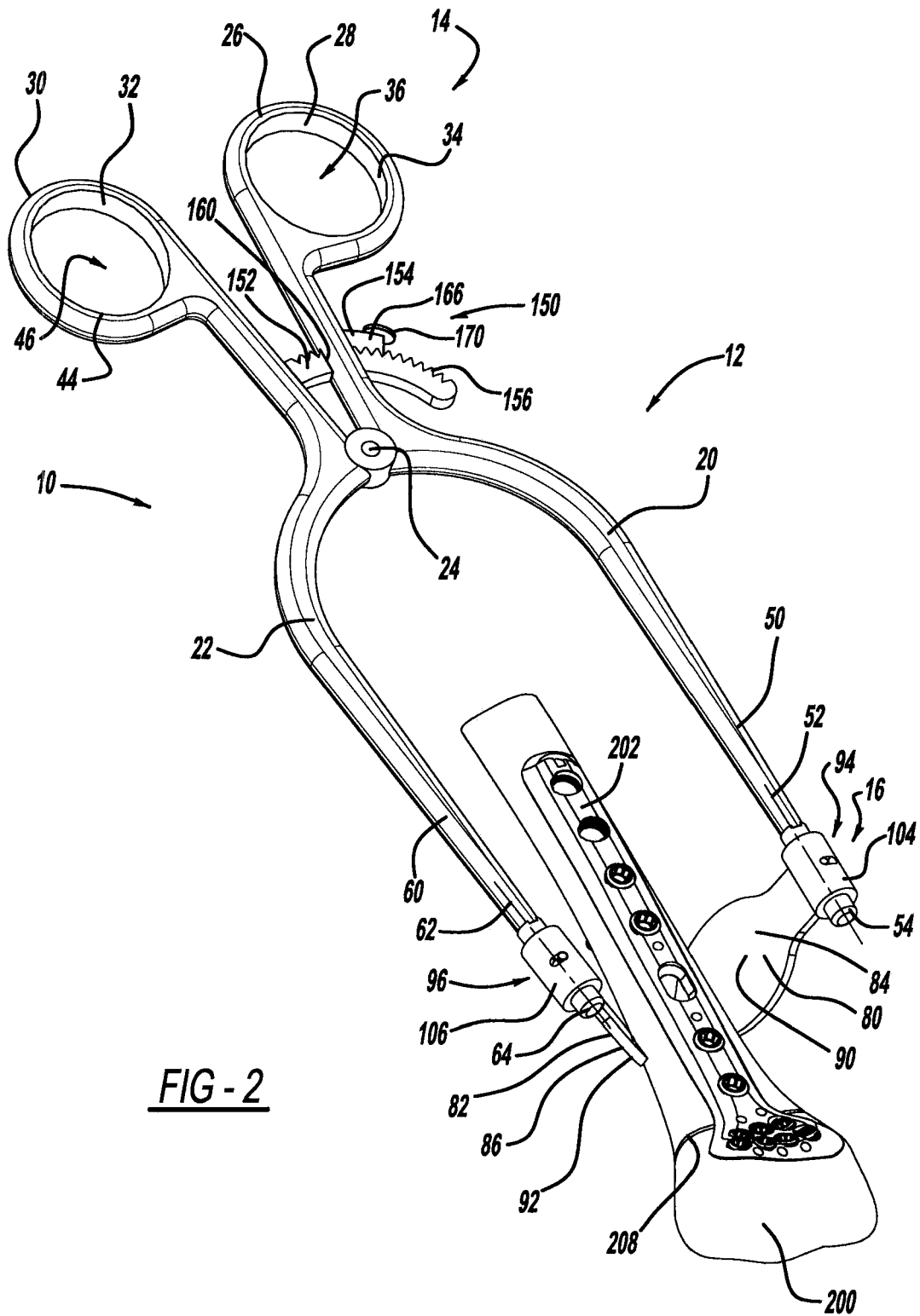
FIG. 2 is a perspective view of the tissue retractor of FIG. 1 and shown with the tissue engaging members rotated to a working position relative to respective arms of the tissue retractor upon urging of a corresponding pair of handles toward each other.
Figure 3:
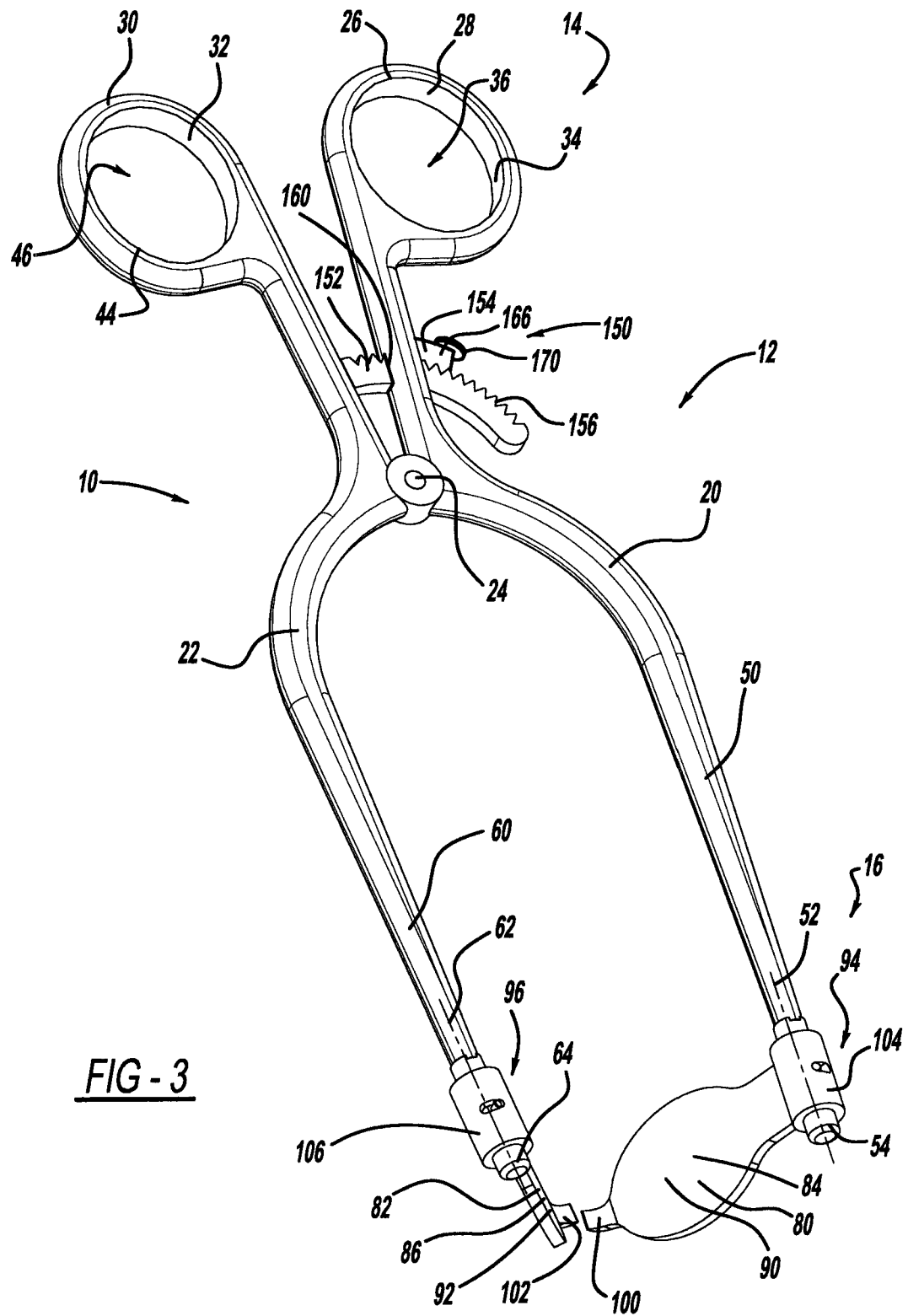
FIG. 3 is another front perspective view of the tissue retractor of FIG. 2 and shown with the tissue engaging members rotated to the working position.

With initial reference now to FIGS. 1-3, a tissue retractor constructed in accordance to one example of the present teachings is shown and generally identified as reference numeral 10. The tissue retractor 10 generally includes an instrument 12 having a user interface portion 14 and a working portion 16 configured at an opposite end. The instrument 12 generally comprises a first arm 20 that is pivotally coupled to a second arm 22 at a pivot 24. The user interface portion 14 can generally include a first handle portion 26 including a finger grip portion 28 formed on the first arm 20 and a second handle portion 30 having a finger grip portion 32 formed on the second arm 22. In the example provided, the finger grip portion 28 includes a closed wall 34 that defines an opening 36 for receiving a finger of a surgeon. Similarly, the finger grip portion 32 can include a closed wall 44 that defines an opening 46 for receiving another finger of a surgeon. Other configurations are contemplated.

Figure 4:
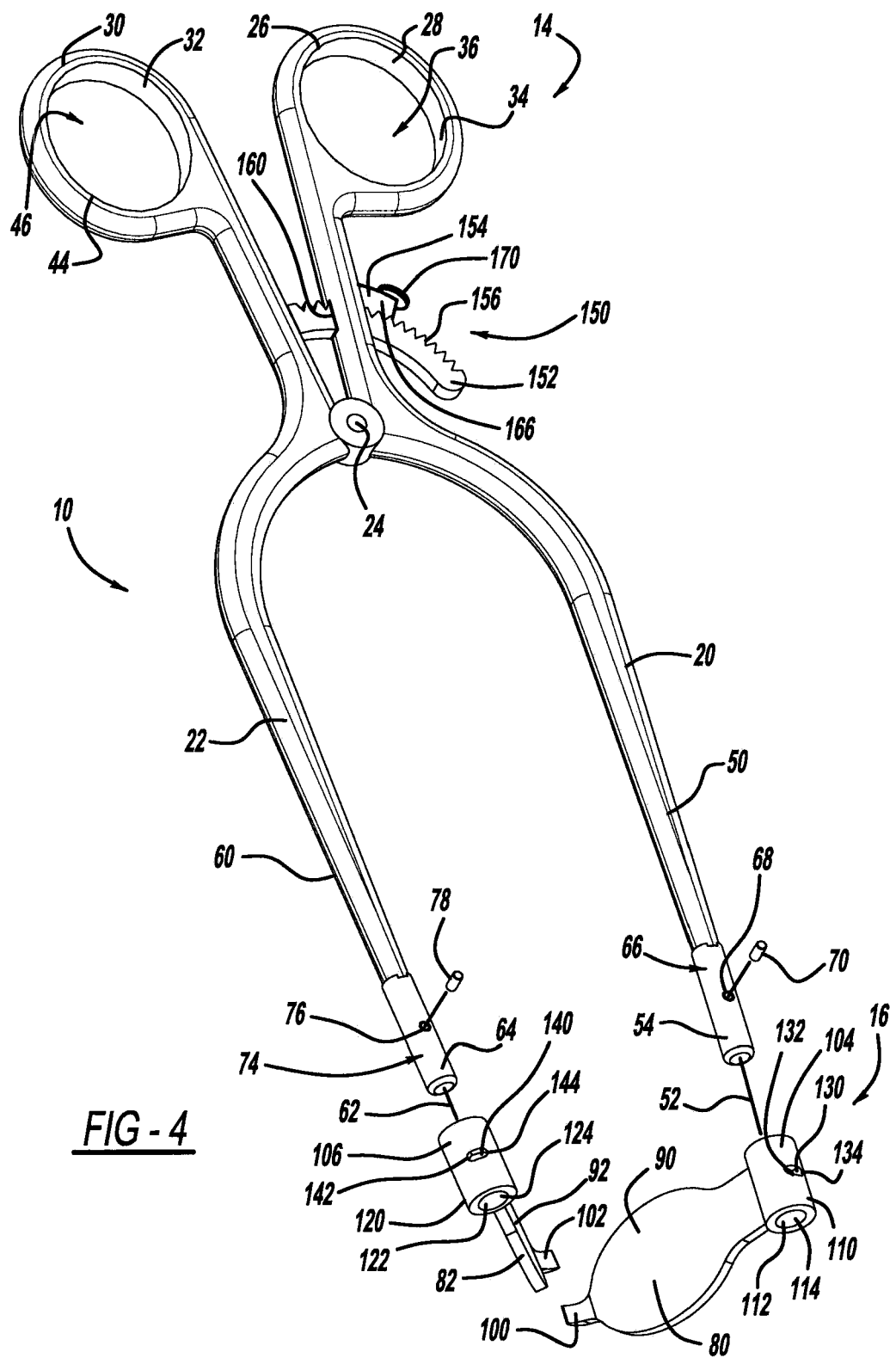
FIG. 4 is an exploded perspective view of the tissue retractor of FIG. 1.

With additional reference now to FIG. 4, additional features of the tissue retractor 10 will be described. The first arm 20 generally includes a first elongated shaft portion 50 having an axis 52. The first elongated shaft portion 50 can terminate at a distal end 54. The second arm 22 can generally include a second elongated shaft portion 60 having an axis 62. The second elongated shaft portion 60 can terminate at a distal end 64. The distal end 54 of the first elongated shaft portion 50 can include an outer surface 66. The outer surface 66 can be generally smooth. A passage 68 can be defined into the distal end 54 for receiving a pin 70. The distal end 64 of the second elongated shaft portion 60 can have an outer surface 74 that is generally smooth. A passage 76 can be formed into the second distal end 64 that receives a pin 78.

With general reference now to FIGS. 1-4, the working portion 16 will be further described. The working portion 16 can collectively include the distal ends 54 and 64 of the respective first and second elongated shaft portions 50 and 60 and corresponding first and second tissue engaging members 80 and 82. The first and second tissue engaging members 80 and 82 are generally in the form of first and second paddles 84 and 86. The paddles 84 and 86 can generally include a planar body portion 90 and 92, respectively that extend between respective mounting portions 94, 96 (FIG. 3) and hooks 100, 102. The mounting portions 94 and 96 generally include a first mounting hub 104 and a second mounting hub 106, respectively.

The first mounting hub 104 generally comprises a cylinder 110 that has an inner surface 112 that defines a throughbore 114. Similarly, the second mounting hub 106 includes a cylinder 120 that has an inner surface 122 that defines a throughbore 124. The first mounting hub 104 is generally journaled around the first distal end 54 of the first elongated shaft portion 50. Similarly, the second mounting hub 106 is generally journaled around the second distal end 64 of the second shaft 60. The outer surface 66 of the first distal end 54 is configured to slidably engage the inner surface 112 of the first mounting hub 104 as the first mounting hub 104 rotates around the axis 52 as will be described herein. Similarly, the outer surface 74 of the second distal end 64 is configured to slidably engage the inner surface 122 of the second mounting hub 106 as the second mounting hub 106 rotates around the axis 62.

The first mounting hub 104 can additionally define a slot 130 that extends between terminal ends 132 and 134. The second mounting hub 106 can further define a slot 140 that extends between terminal ends 142 and 144. The pin 70 is configured to be passed through the slot 130 of the first mounting hub 104 and extended into the passage 68 to rotatably capture the first tissue engaging member 80 onto the first distal end 54 of the first elongated shaft portion 50. Similarly, the pin 78 is configured to be passed through the slot 140 defined in the second mounting hub 106 and be further inserted into the passage 76 on the second distal end 64 of the second shaft 60 to rotatably capture the second tissue engaging member 92 on the second distal end 64 of the second elongated shaft portion 60.

The instrument 12 can additionally include a ratchet assembly 150. The ratchet assembly 150 is generally coupled between the first and second arms 20 and 22. The ratchet assembly 150 comprises a track 152 and a track follower 154. In the example provided, the track 152 is fixedly disposed onto the second arm 22 while the track follower 154 is fixedly disposed onto the first arm 20. It will be appreciated that the location of these components may be reversed. The track 152 generally comprises teeth 156 formed thereon. The track 152 is configured to pass through an opening 160 formed through the first arm 20. The track follower 154 generally includes an engaging body 166 that is configured to selectively engage the teeth 156 upon movement of the respective first and second handle portions 26 and 30 relative to each other. In the particular example provided, the engaging body 166 can be configured to ride along the teeth 156 during movement of the first and second handle portions 26 and 30 toward each other but preclude reverse rotation of the first and second handle portions 26 and 30 by lockingly engaging the teeth 156. Such interaction will therefore block movement of the first and second handle portions away from each other.

The engaging body 166 includes a releasing tab 170 extending therefrom. The releasing tab 170 can be manipulated, such as urged in a direction away from the teeth 156, causing the engaging body 166 to move away from contact with the respective teeth 156. Movement of the releasing tab 170 away from the teeth 156 will allow the first and second handle portions 26 and 30 to move away from each other. Explained further, the tissue engaging members 80 and 82 can move from the working position (FIG. 2) back to the insertion position (FIG. 1).

Figure 5:
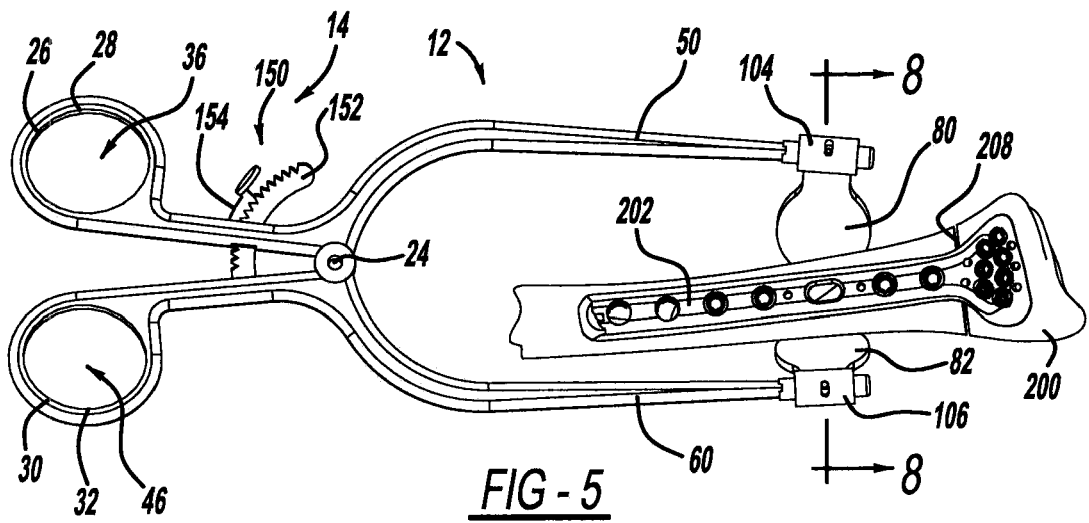
FIG. 5 is a plan view of the tissue retractor of FIG. 2 shown with the handles pivoted toward each other and the tissue engaging members rotated to the working position.

With reference now to FIGS. 6-8, an exemplary method of using the tissue retractor 10 according to one example of the present teachings will be described. The context of the following discussion will be directed toward gaining access to a radius 200 having a bone plate 202 fixed thereon by way of bone screws 204. In the particular example, the bone plate 202 is used to fix a radius 200 that has a fracture 208 (FIG. 5). In this regard, an incision 210 can be prepared on a patient's body 212. It will be appreciated however, that the tissue retractor 10 can be used for spreading tissue to gain access to other parts of a patient's body within the scope of this disclosure.

With specific reference to FIG. 6, the tissue retractor 10 can be initially advanced toward an opening 220 defined by the incision 210. Initially, the hooks 100 and 102 of the respective tissue engaging members 80 and 82 can be advanced through the incision 210 and toward the outer surfaces of the radius 200. The tissue engaging members 80 and 82 of the instrument 12 can be further advanced toward the radius until generally reaching a position shown in FIG. 7 where the hooks 100 and 102 can locate around the radius 200. Notably, the first and second handle portions 26 and 30 of the user interface portion 14 can generally be in the position shown in FIG. 1. It will be appreciated that while the particular mechanical configuration is arranged such that movement of the first and second handle portions 26 and 30 toward each other results in corresponding movement of the distal ends 54 and 64 away from each other, the configuration can be reversed.

Once the tissue engaging members 80 and 82 reach a satisfactory position relative to the radius 200 such as illustrated in FIG. 7, a surgeon moves the first and second handle portions 26 and 30 toward each other (such as to the position shown in FIG. 2) causing the tissue engaging members 80 and 82 to rotate from the insertion position, in FIGS. 6 and 7, to the working position shown in FIG. 8. More specifically, the mounting hubs 104 and 106 are caused to rotate around the outer surfaces 66 and 74 of the respective first and second distal ends 54 and 64. Again, the inner surface 112 of the mounting hub 104 can slidably negotiate around the outer surface 66 such as by way of a clearance fit. Similarly, the inner surface 122 can slidably negotiate around the outer surface 74 of the second distal end 64 by way of a clearance fit.

The mounting hubs 104 and 106 are caused to rotate around the respective axes 52 and 62 of the first and second elongated shaft portions 50 and 60, respectively. In the particular configuration shown, rotation is continued until the pins 70 and 78 engage the terminal ends 132 and 144 (FIG. 8) of the respective slots 130 and 140 defined in the mounting hubs 104 and 106. As illustrated in FIG. 8, an opening 230 results from the tissue engaging members 80 and 82 urging surrounding tissue 232 generally away from each other. Notably, the opening 230 is bigger and provides a more advantageous viewing angle relative to the opening 220 shown in FIG. 6. A larger opening 230 allows the surgeon more space to view, assess and access the area of interest.

Once the size of the opening 230 has been achieved, a surgeon can let go of the user interface portion 14 as the ratchet assembly 150 maintains the first and second arms 20 and 22 of the tissue retractor 10 in a fixed position (or more specifically, the tissue engaging members 80 and 82 in the working position shown in FIG. 8). Again, and as described above, the teeth 156 engage the engaging body 166 such that movement of the first and second handle portions 26 and 30 away from each other is precluded. After the surgeon has successfully performed a procedure relative to the radius 200, a surgeon can move the tissue engaging members 80 and 82 back to the position shown in FIG. 7. In some examples, a biasing member (not specifically shown) can be incorporated on each of the mounting hubs 104 and 106 for urging the tissue engaging members 80 and 82 to the insertion position (FIG. 6). In one example, the surgeon can lift the releasing tab 170 on the track follower 154 and subsequently move the first and second handle portions 26 and 30 toward each other. The tissue retractor 10 can then be removed through the incision 210 of the patient's body 212.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A tissue retractor comprising:
   a pair of arms pivotally coupled to each other and each having a finger grip portion on a first end and a working portion arranged on an opposite second end, wherein each of the second ends comprises an elongated shaft having a longitudinal axis extending axially therethrough; and
   a pair of paddles each having a planar engagement body and a mounting portion pivotally coupled to a corresponding elongated shaft, the paddles being selectively rotatable about the respective longitudinal axes,
   wherein the paddles are coupled to the corresponding elongated shafts such that the paddles are rotationally unbiased relative to the elongated shafts,
   wherein an angle between the respective longitudinal axes changes as the arms pivot relative to each other,
   wherein rotation of the paddles around the respective longitudinal axes is limited to a predetermined range that is less than 360 degrees, and
   wherein each of the paddles includes a mounting hub, each mounting hub includes one of a slot or a pin and each of the elongated shafts includes the other of the slot or the pin, each slot includes terminal ends, and the pins are configured to ride along the corresponding slots and engage the terminal ends, thereby limiting pivoting motion of the paddles relative to the elongated shafts.

2. The tissue retractor of claim 1 wherein each elongated shaft has an outer surface configured to slidably engage a corresponding inner surface of the mounting hub during rotation of the paddles.

3. The tissue retractor of claim 1 wherein the mounting hubs each define one of the slots, and wherein the pins are fixed to a corresponding elongated shaft.

4. The tissue retractor of claim 1, wherein each paddle has a hook extending from a portion of the planar engagement body, the hook extending at an angle relative to the planar engagement body.

5. The tissue retractor of claim 1, further comprising a ratchet assembly coupled between the pair of arms.

6. The tissue retractor of claim 5 wherein the ratchet assembly comprises a track coupled to one of the arms and a track follower extending from the other of the arms, wherein the track follower has an engaging body that cooperatively engages teeth formed on the track.

7. The tissue retractor of claim 6 wherein the engaging body is configured to selectively engage the teeth upon movement of the handle portions toward each other, wherein engagement of the engaging body with the teeth inhibits movement of the finger grip portions away from each other.

8. The tissue retractor of claim 7 wherein the engaging body further includes a releasing tab extending therefrom, wherein movement of the releasing tab disengages contact between the engaging body and the teeth permitting movement of the handle portions away from each other.

9. A tissue retractor comprising:
   a pair of arms pivotally coupled to each other and each having a user interface portion on a first end and a working portion arranged on an opposite second end, wherein each of the second ends comprises an elongated shaft having a longitudinal axis extending axially therethrough; and a pair of tissue engaging members each pivotally coupled to a corresponding elongated shaft, the pair of tissue engaging members having mounting portions that are journalled around the corresponding elongated shafts for rotation about the respective longitudinal axes, wherein the tissue engaging members are coupled to the corresponding elongated shafts such that the tissue engaging members are rotationally unbiased relative to the elongated shafts, wherein an angle between the respective longitudinal axes changes as the arms pivot relative to each other, wherein rotation of the tissue engaging members around the respective longitudinal axes is limited to a predetermined range that is less than 360 degrees, and wherein each of the tissue engaging members includes a mounting hub, each mounting hub includes one of a slot or a pin in each of the elongated shafts includes the other of the slot or the pin, each slot includes terminal ends, and the pins are configures to ride along the corresponding slots and engage the terminal ends, thereby limiting pivoting motion of the paddles relative to the elongated shafts.

10. The tissue retractor of claim 9 wherein each tissue engaging member has a planar body that extends between the mounting portion and a hook extending from an opposite end.

11. The tissue retractor of claim 9 wherein each elongated shaft has an outer surface that is configured to slidably engage a corresponding inner surface of a corresponding mounting hub in an interference fit during rotation of the tissue engaging members.

12. The tissue retractor of claim 11 wherein the mounting hubs each define a slot having terminal ends, wherein a pin fixed to a corresponding elongated shaft is configured to ride along the slot and engage the terminal ends precluding further pivoting of the respective tissue engaging members.

13. The tissue retractor of claim 9, further comprising a ratchet assembly coupled between the pair of arms, the ratchet assembly comprising a track coupled to one of the arms and a track follower extending from the other of the arms, wherein the track follower has an engaging body that cooperatively engages teeth formed on the track.

14. The tissue retractor of claim 13 wherein the engaging body is configured to selectively engage the teeth upon movement of the handle portions toward each other, wherein engagement of the engaging body with the teeth inhibits movement of the user interface portions away from each other.

15. The tissue retractor of claim 14 wherein the engaging body further includes a releasing tab extending therefrom, wherein movement of the releasing tab disengages contact between the engaging body and the teeth permitting movement of the handle portions away from each other.

16. A method of retracting tissue for accessing a bone, the method comprising:

inserting a pair of tissue engaging members into an incision prepared in a patient's body;

positioning hooks extending from distal ends of the tissue engaging members around the bone;

advancing a corresponding pair of handles in directions relative to each other causing the respective pair of tissue engaging members to move away from each other; and further advancing the pair of handles in directions relative to each other causing the respective pair of tissue engaging members to pivot away from each other; and further advancing the pairs of handles in directions relative to each other causing the respective pair of tissue engaging members to pivot about corresponding elongated shafts extending between the respective pair of handles and tissue engaging members, wherein further advancing the pair of handles includes advancing a pin fixedly coupled to each elongated shaft along a slot formed along a mounting hub of a corresponding tissue engaging member until the pin engages a terminal end of the slot inhibiting further rotation of the tissue engaging member.

17. The method of claim 16, wherein each tissue engaging member is mounted to a respective one of the elongated shaft and is pivotable relative to the respective elongated shaft about only a single axis.

* * * * *